US007261707B2

(12) United States Patent
Frezza et al.

(10) Patent No.: US 7,261,707 B2
(45) Date of Patent: Aug. 28, 2007

(54) AMPULE FOR PACKAGING AND TRANSFERRING A LIQUID OR A POWDER FOR MEDICAL USE

(75) Inventors: Pierre Frezza, 455A route du Bas Privas, F-69390 Charly (FR); Alain Botella, Lyons (FR)

(73) Assignee: Pierre Frezza, Charly (FR)

( * ) Notice: Subject to any disclaimer, the term of this patent is extended or adjusted under 35 U.S.C. 154(b) by 257 days.

(21) Appl. No.: 10/450,199

(22) PCT Filed: Dec. 20, 2001

(86) PCT No.: PCT/FR01/04129

§ 371 (c)(1),
(2), (4) Date: Aug. 15, 2003

(87) PCT Pub. No.: WO02/053086

PCT Pub. Date: Jul. 11, 2002

(65) Prior Publication Data

US 2004/0059312 A1 Mar. 25, 2004

(30) Foreign Application Priority Data

Jan. 8, 2001 (FR) .................................. 01 00193

(51) Int. Cl.
*A61B 19/00* (2006.01)
*A61M 5/32* (2006.01)

(52) U.S. Cl. ...................... 604/412; 604/411; 604/416; 604/403

(58) Field of Classification Search ................ 604/403, 604/411–416, 905, 533, 82, 148, 200, 201, 604/243, 244, 192, 110; 206/363–366; 141/329–330
See application file for complete search history.

(56) References Cited

U.S. PATENT DOCUMENTS 3,066,671 A 12/1962 Cohen (Continued)

FOREIGN PATENT DOCUMENTS

EP 255025 A1 * 2/1988

(Continued)

*Primary Examiner*—Tatyana Zalukaeva
*Assistant Examiner*—Leslie R. Deak
(74) *Attorney, Agent, or Firm*—Oliff & Berridge, PLC

(57) ABSTRACT

The invention concerns an ampule comprising a tubular body (2) made of synthetic material having two chambers (3, 4) tightly isolated by a membrane (9) capable of being perforated or a removable or frangible wall, one (31) of which contains the liquid or the powder (6), and the other is accessible from outside to be connected during transfer, the frangible membrane (9) or wall being arranged at the end of a tube (8) integral with the ampule and emerging into the chamber (4) capable of communication with outside, said tube (8) containing a tubular element (14) having a pointed tip (17) oriented towards the membrane. The tubular element (14) and the tube (8) comprise means (13, 16) preventing the tubular element (14) from being separated from the tube (8) after one has been mounted into the other.

24 Claims, 6 Drawing Sheets

U.S. PATENT DOCUMENTS

| | | | | |
|---|---|---|---|---|
| 3,098,481 | A | 7/1963 | Wikander et al. | |
| 3,802,604 | A * | 4/1974 | Morane et al. | 222/83 |
| 4,089,432 | A * | 5/1978 | Crankshaw et al. | 215/6 |
| 5,445,630 | A * | 8/1995 | Richmond | 604/411 |
| 5,445,631 | A * | 8/1995 | Uchida | 604/412 |
| 5,772,652 | A * | 6/1998 | Zielinski | 604/411 |
| 6,003,566 | A | 12/1999 | Thibault et al. | |
| 6,070,623 | A * | 6/2000 | Aneas | 141/329 |
| 6,253,804 | B1 * | 7/2001 | Safabash | 141/97 |
| 6,258,078 | B1 * | 7/2001 | Thilly | 604/411 |
| 6,537,263 | B1 * | 3/2003 | Aneas | 604/412 |
| 6,706,031 | B2 * | 3/2004 | Manera | 604/411 |

FOREIGN PATENT DOCUMENTS

| | | |
|---|---|---|
| EP | 0 499 764 A1 | 8/1992 |
| FR | 2 788 431 | 7/2000 |
| FR | 2 791 254 | 9/2000 |
| GB | 528471 | 10/1940 |
| WO | WO 00/15292 | 3/2000 |

* cited by examiner

AMPULE FOR PACKAGING AND TRANSFERRING A LIQUID OR A POWDER FOR MEDICAL USE

The subject of the present invention is an ampule for packaging and transferring a liquid or a powder, for medical use, in a container.

Devices exist for transferring a liquid stored in a sealed container to a drip bag or for transferring a freeze-dried or other type of powder, once it has been reconstituted into liquid form, to a drip bag.

Drip bags are generally equipped with an injection site formed of a tube connected to the contents of the bag and closed by a puncturable film or by a valve device. Valve devices are generally housed in the end of a female LUER Lock hub. The valve opens automatically when a male LUER Lock is connected.

The existing devices are intended to improve patient safety by reducing the risks of bacteriological contamination, and to improve operator safety by reducing the risks of needle-stick injuries and the inhalation of toxic products.

The existing devices are all in the form of a preassembled system for clipping onto a standard-size glass bottle equipped with a stopper, puncturable or otherwise, depending on the device.

The use of glass bottles entails specific operating means, and leads to a high cost. Furthermore, the use of glass poses a problem because of the risk of breakage, which may have serious consequences when the medicinal product is dangerous, as is the case of medicinal products used to treat cancer.

Document FR 2 791 254 in the name of the Applicant describes an ampule for packaging a liquid for medical use. That device comprises a needle of the hypodermic type, the point of which faces toward a puncturable membrane and the other end of which is equipped with means of connection to a medical syringe. That device can be used only in conjunction with a syringe.

Now, in a certain number of medical applications, there is no need to meter out drugs aspirated from the ampule and seen against the graduations of the syringe, particularly when the issue is one of transferring the entire contents of an ampule to a drip bag.

The object of the invention is therefore to provide an ampule for packaging and transferring a liquid or a powder into a bag for medical use, which is self-sufficient and does not require the use of an intermediate syringe. The ampule according to the invention needs to be an ampule of simple structure, entailing no use of means other than those contained in the ampule, and affording complete safety to patients and operators, by, in particular, preventing certain constituent parts of the ampule from being able, while the liquid or the powder is being transferred, or after the liquid or the powder has been transferred, to contaminate the patients or care staff.

To this end, the ampule to which it relates, comprising a tubular body made of synthetic material having two chambers isolated in a sealed manner by a puncturable membrane or a removable or frangible wall, one of which chambers contains the liquid or powder and the other of which chambers is accessible from the outside to establish a connection at the time of transfer, the puncturable wall or membrane being arranged at the end of a tube secured to the ampule and opening into the chamber, which can be placed in communication with the outside, this tube containing a tubular element having a pointed end facing toward the membrane and being movable over a distance at least equal to that necessary to puncture the membrane, is characterized in that the tubular element and the tube comprise means preventing the tubular element and the tube from being separated once one has been mounted in the other. As the ampule is made from synthetic material, the risks of its breaking are excluded. Furthermore, the ampule incorporates the means for transferring to a bag, these means consisting of the tubular element mounted to slide in the tube that the ampule comprises. The use of this ampule avoids any risk to the medical staff, because the tubular element cannot be separated from the tube once it has been mounted in the latter.

According to one feature of the invention, the means preventing the tubular element and the tube from being separated consist of a shoulder formed at the periphery of the tubular element and at least one projecting part formed on the internal face of the tube. Advantageously, the tubular element and the tube are each equipped with an annular shoulder forming the separation-preventing means. The annular shoulder of the tubular element also provides sealing with respect to the tube, once the membrane has been punctured.

This separation of the tubular element from the tube can be obtained before or after the membrane has been punctured, the essential point being that the tubular element cannot be separated from the tube once the product has been transferred.

In order to improve the robustness of the tubular element and the seal between the tubular element and the tube, the part of the tubular element situated toward the pointed end is of frustoconical shape, complementing that of the corresponding part of the tube, in which part the tubular element is engaged in the position in which the membrane has been punctured.

There are various possible forms of embodiment of this ampule.

According to a first embodiment, the second end of the tubular element is also pointed.

Advantageously, in this case, the tubular element comprises, toward its second end, a part that, in the storage position, protrudes beyond the tube by an amount at least equal to the amount by which the tubular element moves.

According to another embodiment of this ampule, the second end of the tubular element is in the form of a coupling, such as a male LUER hub.

To make connection to a bag easier, the tube has an internal screw thread for a threaded coupling intended to be fixed with sealing onto the second end of the tubular element.

To prevent the tubular element and the tube from turning while the connection is being made, the tubular element and the tube comprise complementary rotation-proofing fins.

According to another embodiment of this ampule, the region of the tube located away from that equipped with the membrane is shaped as a coupling of the female LUER type.

Advantageously, in this case, and in order to ensure a good coupling of the container to the ampule, this end of the tube has an external screw thread for an internally threaded coupling intended to be fixed with sealing onto the tube and comprising an internal part in the form of a LUER hub, engaged in the tube and resting against the end of the tubular element.

According to one feature of the invention, the chamber not containing the liquid or the powder is closed. This closure may be achieved using a peelable film or using a cap.

According to another embodiment of this ampule, the ampule is made of flexible synthetic material and the chamber containing the liquid or the powder is closed by flattening and heat-sealing.

According to another embodiment of this ampule, the ampule is made of rigid synthetic material and the chamber containing the liquid or the powder is closed by an attached stopper.

The stopper may also be produced in the form of a container for the medicinal product. The heat-sealing weld in this case will be offset toward the central part of the body.

According to one embodiment of this ampule, when the end region of the tube at the opposite end from that equipped with the membrane is shaped as a coupling of the female LUER type, this end of the tube has an external screw thread for an internally threaded coupling intended to be fixed with sealing onto the tube and comprising an internal part in the form of a LUER hub, engaged in the tube and resting against the end of the tubular element.

This last embodiment allows fitting to any type of container, particularly glass bottles or injection sites that are not fixed at the end of a tube.

In any event, the invention will be clearly understood with the aid of the description that follows, with reference to the attached schematic drawings that, by way of nonlimiting examples, depict several embodiments of this ampule.

Figure 1:
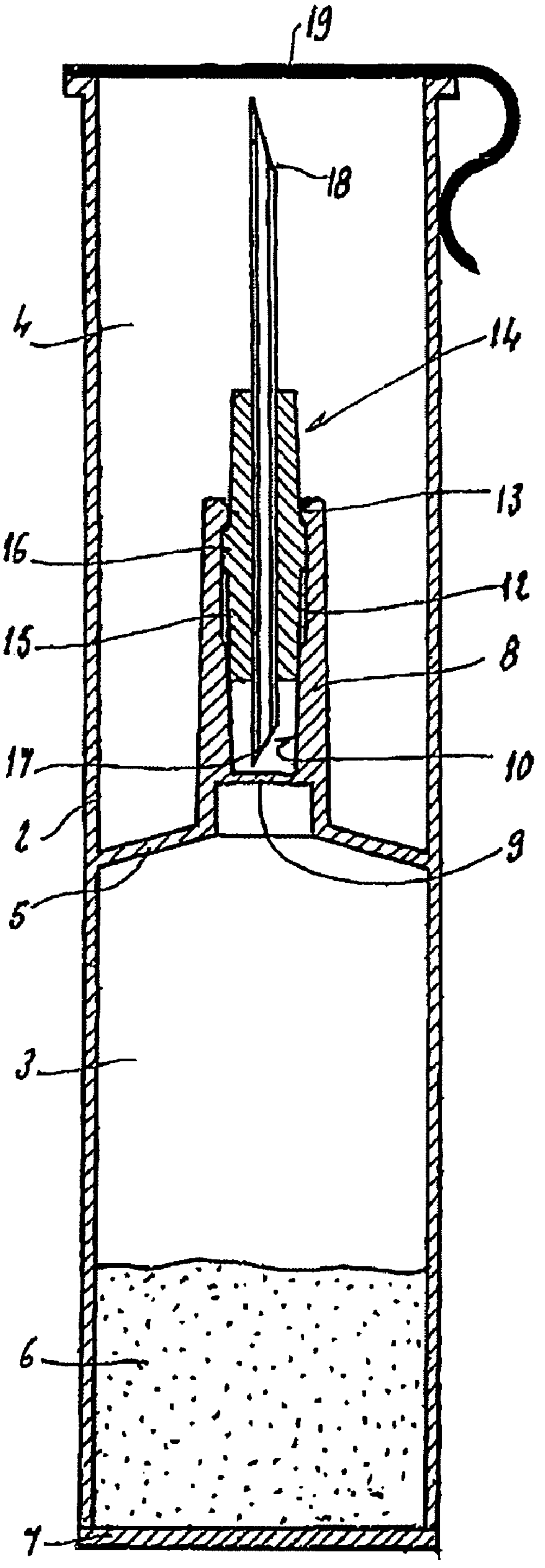
FIG. 1 is a view in longitudinal section of a first ampule.

The ampule depicted in FIG. 1 comprises a cylindrical tubular body 2 made of synthetic material, having two chambers, a lower chamber 3 and an upper chamber 4, separated from one another by a partition 5 in the form of a disk. The chamber 3 contains a product such as a liquid or a powder 6 and is closed off by an end wall 7 fixed, for example, by heat welding. Extending from the partition 5 is a tube 8 that is closed off near the partition 5 by a puncturable membrane 9. The tube 8 on its interior face and near the membrane 9 comprises a frustoconical part 10 extended by a tubular part comprising an annular recess 12 bounded, near the free end of the tube, by an annular shoulder 13. Associated with the tube 8 is a tubular element 14 comprising a front part 15 of frustoconical shape, complementing the frustoconical part 10 of the tube and a peripheral annular shoulder 16 intended to bear with sealing in the annular recess 12 and to come into abutment against the shoulder 13 of the tube to prevent any risk of the tubular element being extracted. This tubular element has two points 17 and 18 facing one toward the membrane and the other toward the outside. In the embodiment depicted in the drawing, when the point 17 is set back from the membrane 9, as shown in FIG. 1, the tubular element 14 cannot be extracted from the tube because the shoulders 16 and 13 are resting against each other. The chamber 4 is closed off by a peelable film 19.

A connection is intended to be made with a bag 20, just part of which is depicted in the drawing, ending in a nozzle 22 equipped with a filling site 23 equipped with a puncturable stopper 24.

The use of the ampule depicted in FIGS. 1 to 5 is as follows:

The film 19 is torn off. The point 18 of the tubular element 14 is offered up to the center of the stopper 24 of the bag 20. If the stopper of the injection site of the bag is easy to puncture, the point 18 will puncture it before the point 17 punctures the membrane 9 of the ampule. However, liquid cannot flow out because of the sealing means 16. With the pressure sustained, the end of the injection site 22, 23 will come up close to the part of the tubular element 14 protruding from the tube 8. The tubular element will then puncture the membrane 9 to make the communication between the two volumes. This is the position depicted in FIG. 4. The operator then exerts presses repeatedly on the flexible bag, allowing the liquid to flow from the bag to the ampule and the air contained in the ampule to flow into the bag. If the ampule contains powder, the powder can thus be dissolved in the liquid thus taken up. When the powder is fully dissolved, the operator inverts the assembly, the ampule being at the top and the bag at the bottom, and resumes the pumping action by pressing successively on the flexible bag. The liquid contained in the ampule passes into the bag and is replaced with the air contained in the latter. Once the operation is over, the operator uncouples the bag and the ampule, the tubular element 14 remaining captive in the ampule, thus avoiding any risk of contamination.

If the ampule contains a medicinal product in liquid form, only the second operation need be performed in order to transfer the liquid to the bag.

Figures 6, 7, 8:
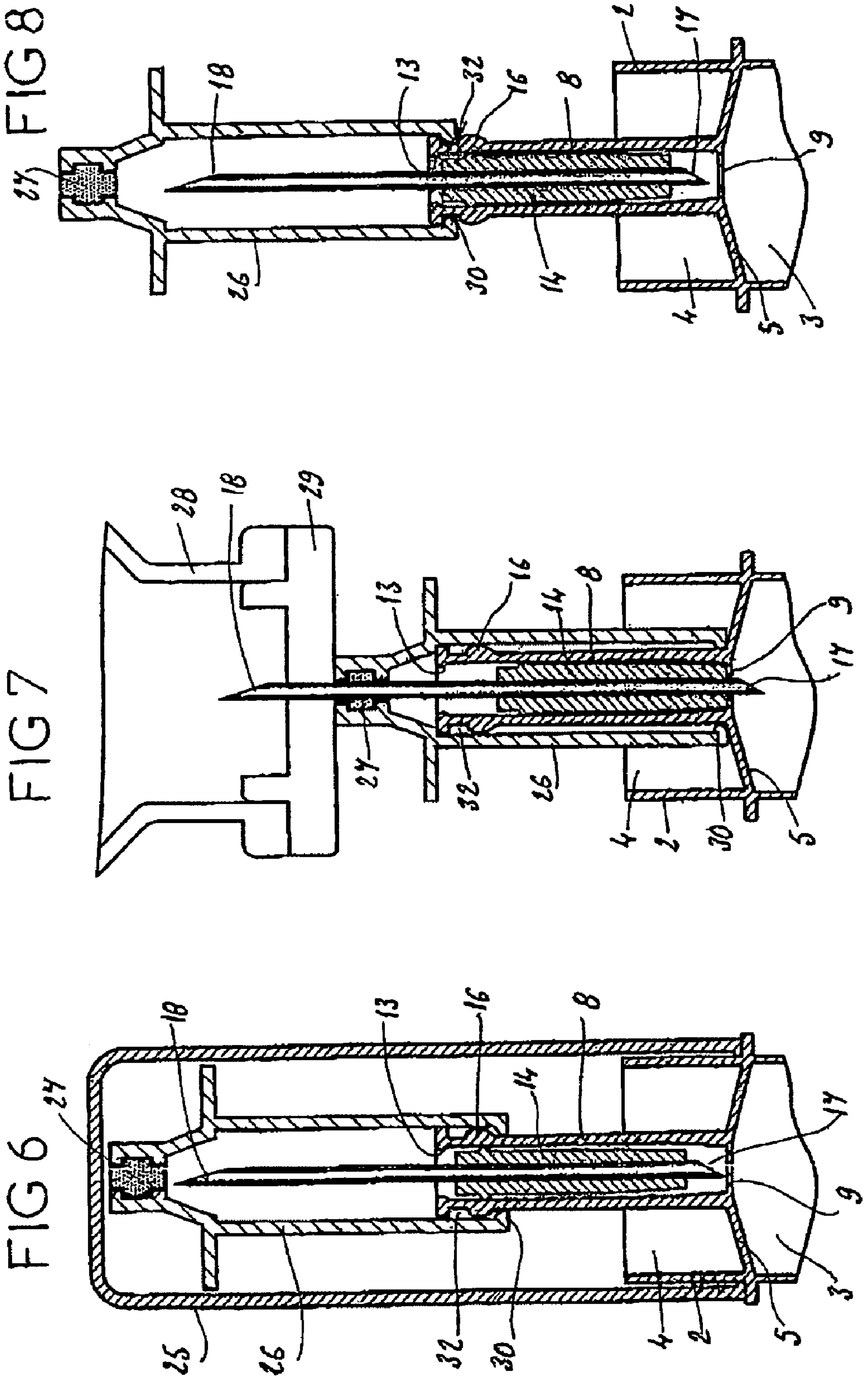
FIGS. 6 to 8 are three views of an alternative form of embodiment of the ampule of FIGS. 1 to 5, during three phases of use.

In the embodiment depicted in FIGS. 6 to 8, in which the same elements are denoted by the same references as previously, the tube 8 protrudes beyond the second chamber 4. In the position of non-use, the ampule is closed by a cap 25. In this embodiment, a second tube 26 is mounted to slide on the first tube 8. The end of this second tube 26 may be closed off by a stopper 27.

This ampule is aimed essentially at transferring the contents of the ampule to a bottle 28 that is not equipped with a connecting tube but is simply closed by a puncturable stopper 29.

In this case, the operator, having removed the protective cap 25, presses the stopper 27 against the stopper 29 of the bottle. With the ampule held by the operator, pressure is exerted toward the bottle 28 to cause the tube 26 to slide on the tube 8, thus allowing the point 18 to puncture the stoppers 27 and 29 in succession, and allowing the point 17 to puncture the membrane 9. This is depicted in FIG. 7. As the contents of the ampule are in communication with the contents of the bottle or of the bag, reconstitution can be performed in the way indicated previously, the pumping action being performed by the ampule.

At the end of the procedure, the operator pulls on the body of the ampule, holding the tube 26 still, and this has the effect of causing the tube 26 to cover the point 18 and then of locking this tube through the collaboration of a shoulder 30 of the tube 26 with a groove 32 of the tube 8, as shown in FIG. 8. The needle is thus protected after use. If the membrane 27 is chosen to be of a self-sealing material, the chamber 3 is isolated in a sealed manner from the outside, thus avoiding harmful emanations when the medicinal product is dangerous to the care staff.

Figure 5:
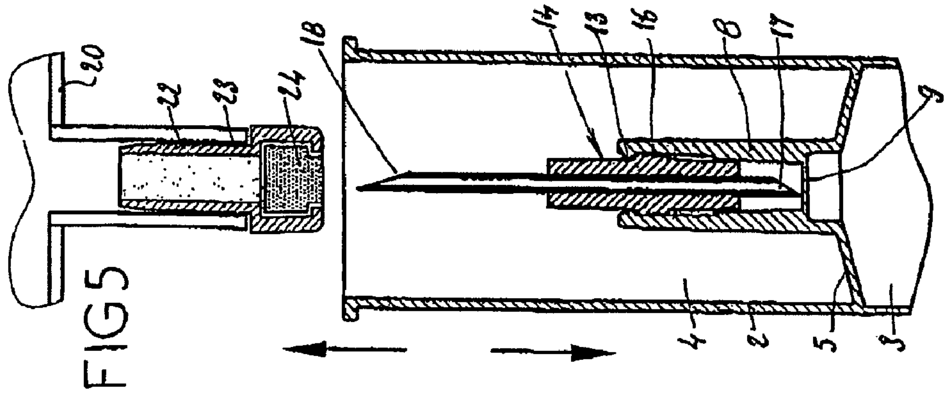
FIGS. 2 to 5 are part views in longitudinal section of the same ampule during several successive phases of use.
Figure 4:
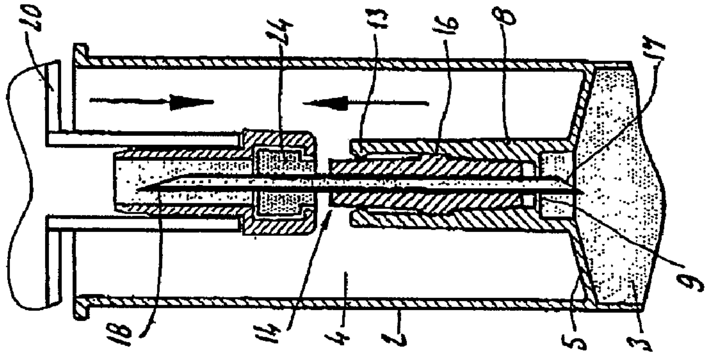
Figure 3:
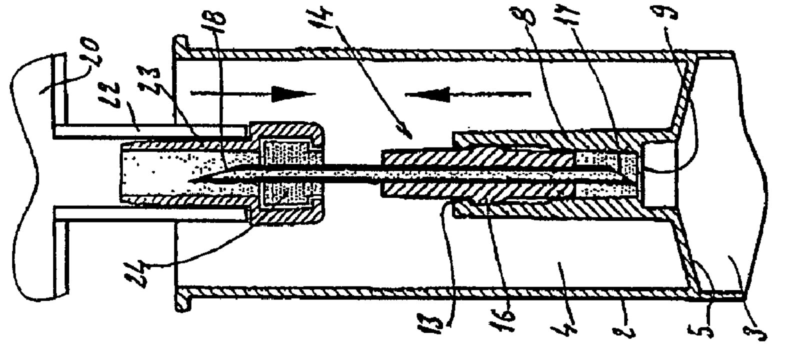

As a preference, and as is the case in the two embodiments mentioned hereinabove, the ampule comprises protective means preventing the user from accessing the point 18, so as to avoid any injury or contamination. In the first embodiment mentioned, protection is afforded by the tubular body 2 forming the second chamber 4, which surrounds and protrudes beyond the point 18, even when the element 8 is in the high position and the shoulders 13 and 16 are in abutment against each other, as illustrated in FIG. 5. In the second embodiment, the protective means are formed by the protective tube 26 that covers the transfer element, particularly the point 18, at all times, except when a bottle or a bag is connected to the ampule, as is illustrated in FIGS. 6, 7, and 8.

FIGS. 9 through 13 depict another embodiment in which the same elements are denoted by the same references as previously.

In this embodiment, the end of the tubular element 14, the opposite end from the point 17, consists of a male LUER hub 35. The rear end of the tube 8 has a screw thread 36. The front end of the tubular element 14 has fins 37 complementing fins 38 formed in the tube 8 near the membrane 9. These fins are aimed at preventing the tubular element from turning with respect to the tube in the position in which the membrane has been perforated. In the embodiment depicted, a bag 39 is equipped with a site 40 with a valve associated with a female LUER hub 42 intended to engage with the male LUER hub of the tubular element.

Figure 2:
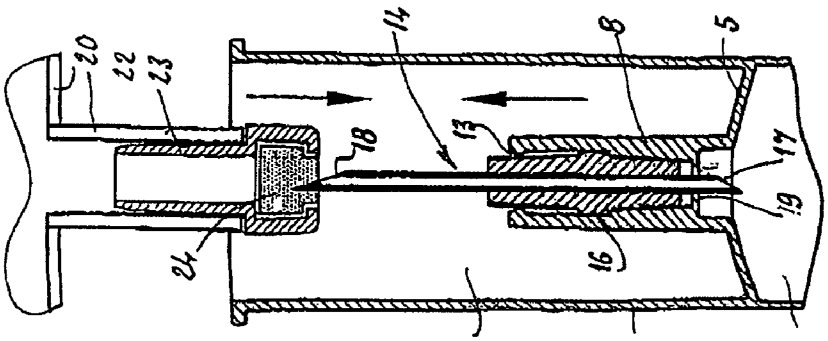
Figure 11:
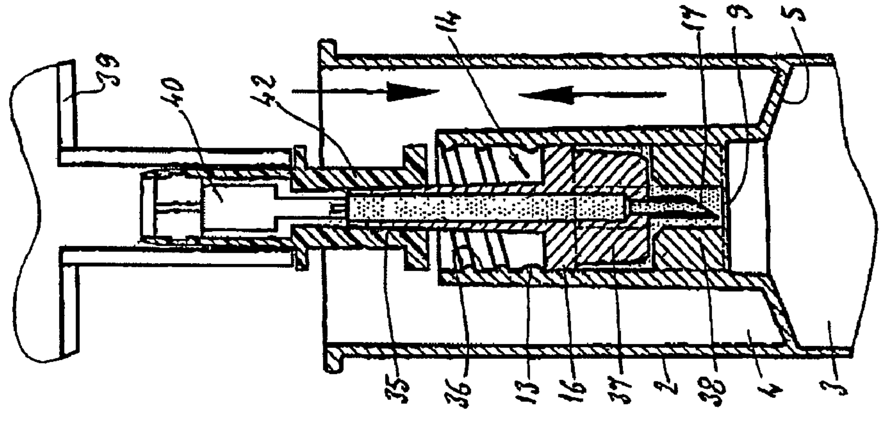
FIGS. 9 to 13 are five views of another ampule in the course of five phases of use.
Figure 10:
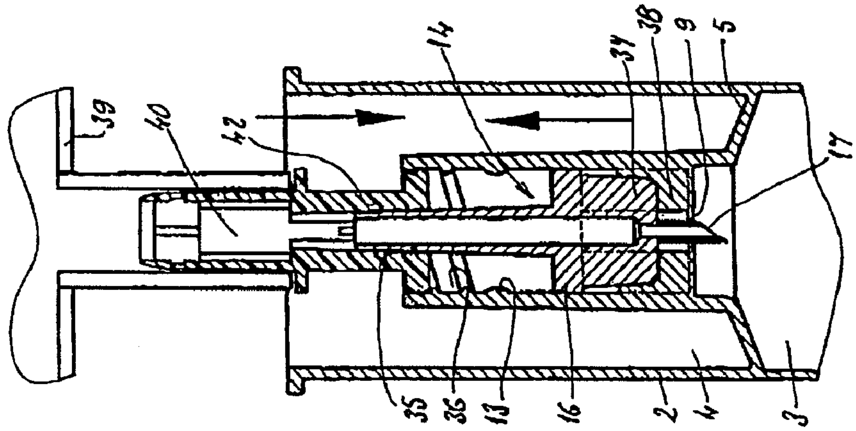
Figure 9:
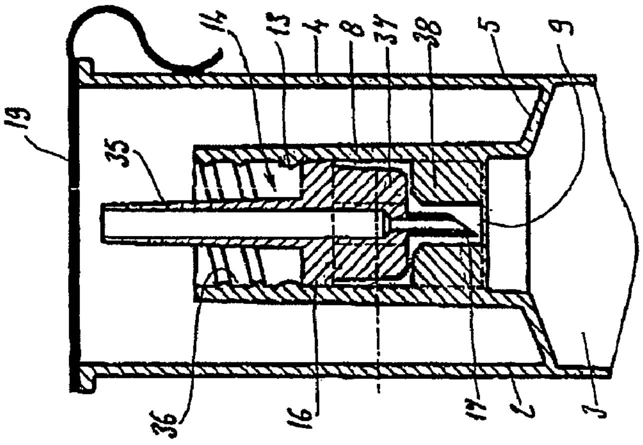
Figure 12:
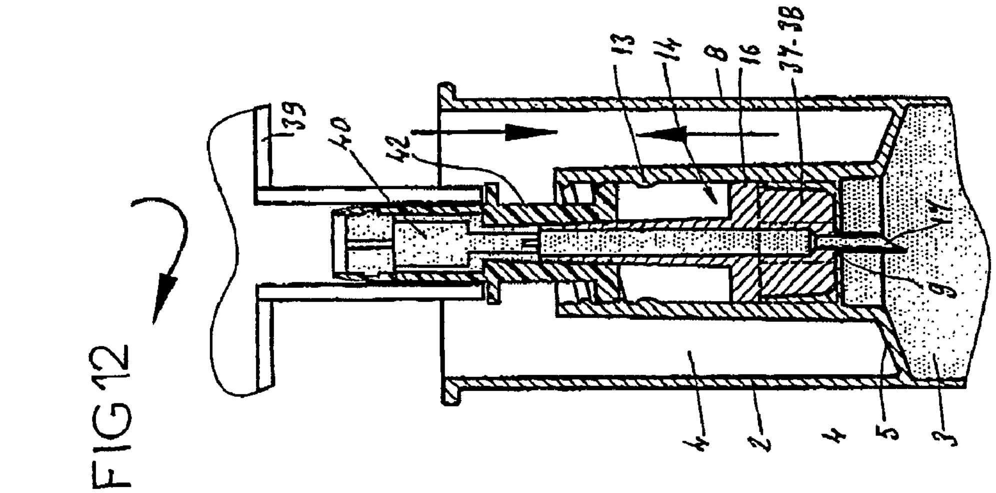
Figure 14:
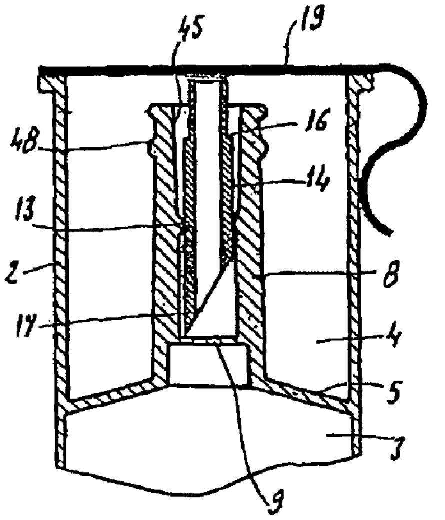
FIGS. 14 to 17 are four views in longitudinal section of another ampule, during four phases of use.

This ampule is used as follows:

Having torn off the film 19, the site 42 of the bag 39 is engaged on the LUER hub 35 of the element 14, and screwed into the internal screw thread 36 of the tube 8. This connecting movement is depicted in FIG. 2, where the membrane is punctured first of all. It is also possible to imagine the scenario where coupling between the bag and the tubular element is achieved before the membrane is punctured, as shown in FIG. 11. FIG. 12 shows the ampule and the bag in the connected position, from which position transfer of the liquid or powder from one container to the other can be achieved in the way mentioned earlier.

Figure 13:
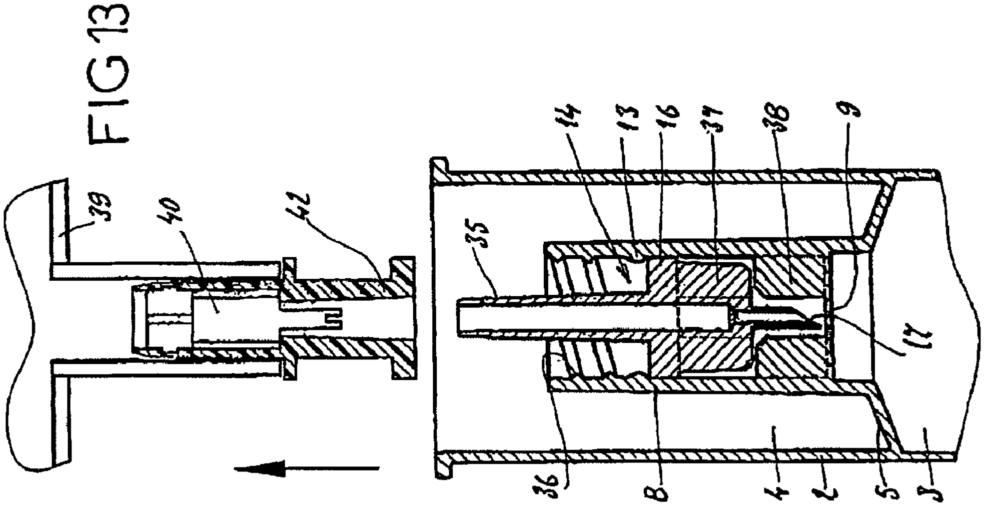

At the end of the transfer, and as shown in FIG. 13, the bag is disconnected, having been unscrewed from its site, the tubular element 14 remaining held in the tube 8, as shown in FIG. 13.

FIGS. 14 to 17 depict another form of embodiment of this ampule in which embodiment the same elements are denoted by the same references as previously.

In this case, the outer end of the tube 8 is shaped as a female LUER hub 35 able to accommodate, with sealing, a male LUER hub 46 of a container 47 or of a syringe, bearing with sealing against the posterior end of the tubular element 14. To provide conditions for connection, the tube 8 may have an external screw thread 48 onto which an internally threaded part 49 belonging to the neck of the container 47 is screwed.

Figure 15:
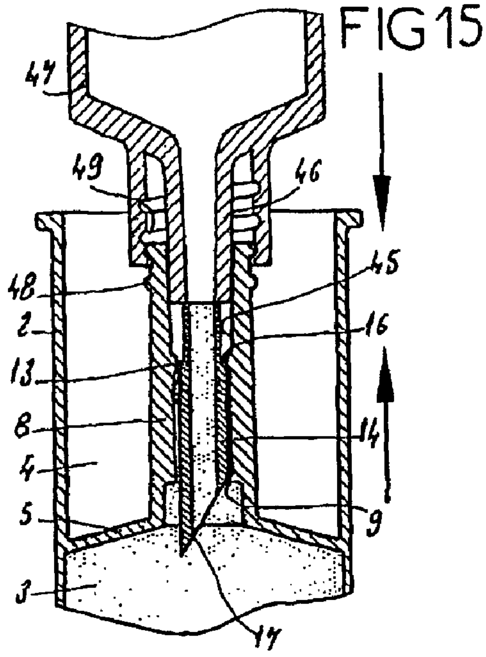
Figure 16:
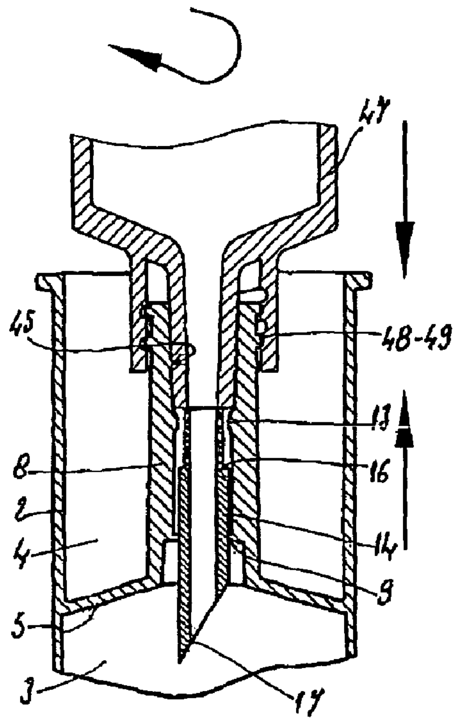
Figure 17:
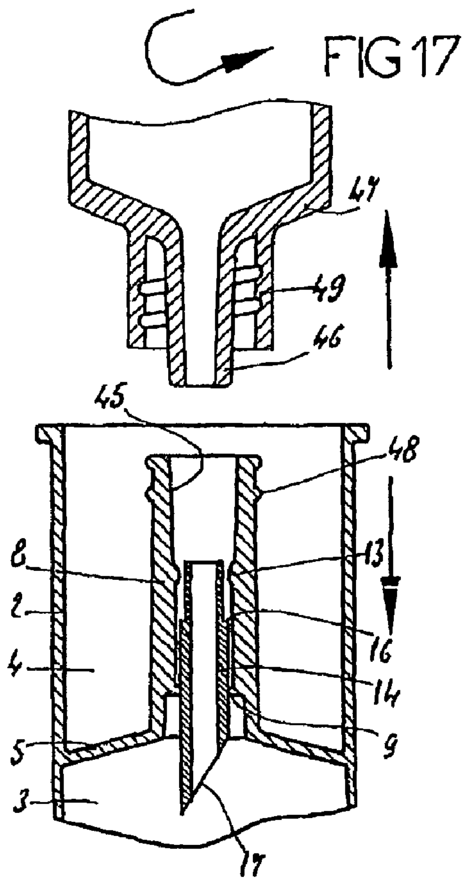

As the neck is screwed onto the tube 8, the female LUER hub 45 and male LUER hub 46 become coupled and the end of the male LUER hub 46 pushes against the tubular element 14 to puncture the membrane 9 as shown in FIG. 15. FIG. 16 depicts the end of connection, from where transfer can begin. Uncoupling is achieved by unscrewing, as shown in FIG. 17, the tubular element 14 remaining captive in the tube 8.

As is apparent from the foregoing, the invention makes a great improvement to the existing art by providing an ampule, intended for packaging and transferring a liquid or a powder to a bag or another container, of a simple structure, incorporating the transfer means and retaining these after transfer, thus avoiding the risks of contamination both as far as the patient is concerned and as far as the operator is concerned.

As goes without saying, the invention is not restricted solely to the embodiments of this ampule described hereinabove by way of examples; on the contrary, it encompasses all alternative forms thereof. Thus, in particular, the ampule could be made of a flexible synthetic material and the chamber 3 containing the liquid or the powder could be closed off not by an end wall but by pinching together the material of which the body is made and heat-sealing it, without in any way departing from the scope of the invention.

The invention claimed is:

1. An ampule for packaging and transferring a liquid or a powder for medical use in a container, comprising:

a tubular body made of synthetic material exhibiting two chambers isolated in a sealed manner by a puncturable membrane or a removable or frangible wall, one of which chambers contains the liquid or powder and the other of which chambers is accessible from the outside to establish a connection at the time of transfer, wherein the two chambers and the tubular body are one unitary piece;

the puncturable wall or membrane being arranged at the end of a tube secured to the ampule and opening into the chamber which can be placed in communication with the outside, this tube containing a tubular element having a pointed end facing toward the membrane and being movable over a distance at least equal to that necessary to puncture the membrane, wherein the tubular element and the tube comprise means preventing the tubular element and the tube from being separated once one has been mounted in the other and also provides sealing between the tubular element and the tube once the membrane has been punctured.

2. The ampule as claimed in claim 1, wherein the means preventing the tubular element and the tube from being separated consist of a shoulder formed at the periphery of the tubular element and at least one projecting part formed on the internal face of the tube.

3. The ampule as claimed in claim 2, wherein the tubular element and the tube are each equipped with an annular shoulder forming the separation-preventing means.

4. The ampule as claimed in claim 2, wherein the means preventing separation are designed to prevent the tubular element and the tube from being separated in the position in which the membrane is not punctured.

5. The ampule as claimed in claim 2, wherein the means preventing separation are designed to prevent the tubular element and the tube from being separated in the position in which the membrane has been punctured.

6. The ampule as claimed in claim 1, wherein the part of the tubular element situated toward the pointed end is of frustoconical shape, complementing that of the corresponding part of the tube, in which part the tubular element is engaged in the position in which the membrane has been punctured.

7. The ampule as claimed in claim 1, wherein the tubular element comprises means of sealing with respect to the tube.

8. The ampule as claimed in claim 7, wherein the sealing means consist of the means that also hold the tubular element in the tube.

9. The ampule as claimed in claim 1, wherein the second end of the tubular element is also pointed.

10. The ampule as claimed in claim 9, wherein the tubular element comprises, toward its second end, a part that, in the storage position, protrudes beyond the tube by an amount at least equal to the amount by which the tubular element moves.

11. The ampule as claimed in claim 9, wherein the tube protrudes beyond the chamber not containing the liquid or the powder and serves to guide the sliding of a second tube covering the point of the second end of the tubular element.

12. The ampule as claimed in claim 11, wherein the second tube is equipped, at its end, with a membrane or stopper that can be punctured by the second point of the tubular element.

13. The ampule as claimed in claim 9, further comprising a protective means preventing the user from accessing the point.

14. The ampule as claimed in claim 13, wherein the protective means are formed by the tubular body forming the second chamber, which surrounds and protrudes beyond the point, even when the element is in the high position and the shoulders are in abutment against each other.

15. The ampule as claimed in claim 13, wherein the protective means are formed by the protective tube that covers the point except when a bottle or a bag is connected to the ampule.

16. The ampule as claimed in claim 1, wherein the second end of the tubular element is in the form of a coupling, such as a male LUER hub.

17. The ampule as claimed in claim 16, wherein the tube has an internal screw thread for a threaded coupling intended to be fixed with sealing onto the second end of the tubular element.

18. The ampule as claimed in claim 17, wherein the tubular element and the tube have complementary rotation-proofing fins.

19. The ampule as claimed in claim 1, wherein a region of the tube located away from that equipped with the membrane is shaped as a coupling of the female LUER type.

20. The ampule as claimed in claim 19, wherein the region of the tube has an external screw thread for an internally threaded coupling intended to be fixed with sealing onto the tube and comprising an internal part in the form of a LUER hub, engaged in the tube and resting against the end of the tubular element.

21. The ampule as claimed in claim 1, wherein the chamber not containing the liquid or the powder is closed by a peelable film.

22. The ampule as claimed in claim 1, wherein the chamber not containing the liquid or the powder is closed by a cap.

23. The ampule as claimed in claim 1, wherein the ampule is made of flexible synthetic material and the chamber containing the liquid or the powder is closed by flattening and heat-sealing.

24. The ampule as claimed in claim 1, wherein the ampule is made of rigid synthetic material and the chamber containing the liquid or the powder is closed by an attached stopper.

* * * * *